United States Patent [19]

Aigami et al.

[11] 3,962,328

[45] June 8, 1976

[54] ADAMANTYL THIOAMIDES

[75] Inventors: Koji Aigami; Yoshiaki Inamoto, both of Wakayama, Japan

[73] Assignee: Kao Soap Co., Ltd., Tokyo, Japan

[22] Filed: Apr. 28, 1975

[21] Appl. No.: 572,355

[30] Foreign Application Priority Data
May 1, 1974 Japan.............................. 49-49067
Dec. 26, 1974 Japan.............................. 50-1723

[52] U.S. Cl.............................. 260/551 S; 260/464; 260/557 B; 424/320
[51] Int. Cl.²..................................... C07C 153/057
[58] Field of Search......... 260/551 S, 557 B, 326.39

[56] References Cited
UNITED STATES PATENTS

| | | | |
|---|---|---|---|
| 3,274,243 | 9/1966 | Gilbert et al. ................. | 260/551 S |
| 3,346,632 | 10/1967 | Tull et al. ...................... | 260/551 S |
| 3,534,086 | 10/1970 | Narayanan et al............. | 260/490 |
| 3,624,126 | 11/1971 | Narayanan..................... | 260/464 X |
| 3,657,273 | 4/1972 | Krimmel........................ | 260/557 B X |
| 3,663,565 | 5/1972 | Krimmel........................ | 260/326.39 X |
| 3,748,359 | 7/1973 | Thompson..................... | 260/464 X |
| 3,816,509 | 6/1974 | Krimmel........................ | 260/326.39 X |
| 3,821,275 | 6/1974 | Inamoto et al................. | 260/557 B X |

OTHER PUBLICATIONS
Neovadba et al., CA 79;136909s, (1973 – German Offen. 2,306,784, Aug. 30, 1973, pp. 1 and 4 enclosed).

*Primary Examiner*—Robert V. Hines
*Assistant Examiner*—Thomas A. Waltz
*Attorney, Agent, or Firm*—Woodhams, Blanchard and Flynn

[57] ABSTRACT

Adamantyl thioamides having the formula:

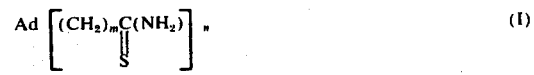

(I)

in which Ad is adamantyl or alkyl-substituted adamantyl; $m$ is a number of 0 or 1, $n$ is a number of 1 or 2, with the proviso that $m$ is 1, when $n$ is 2; and the aminothiocarbonylmethyl or the aminothiocarbonyl group is bonded to a bridgehead carbon atom of the adamantane ring, are prepared by reacting a nitrile having the formula

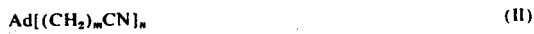 (II)

in which Ad, $m$ and $n$ have the same meaning as above, with hydrogen sulfide in the presence of a catalyst. The compounds possess antiviral activity.

1 Claim, No Drawings

ADAMANTYL THIOAMIDES

BACKGROUND OF THE INVENTION

Field of the Invention

This invention relates to adamantyl thioamides and a process for preparing those compounds, said adamantyl thioamides having the formula

in which Ad is adamantyl or alkyl-substituted adamantyl; $m$ is a number of zero or one, $n$ is a number of one or 2, with the proviso that when $n$ is 2, m is one; and the aminothiocarbonylmethyl or the aminothiocarbonyl group is bonded to a bridgehead carbon atom of the adamantane ring.

Compounds of the formula (I) are believed to be novel substances which are not disclosed in the prior art. These compounds are valuable not only as intermediates for the synthesis of adamantane-substituted heterocyclic compounds but also as substances having an excellent anti-viral activity, especially an excellent effect of preventing propagation of Newcastle disease virus.

SUMMARY OF THE INVENTION

We have discovered that when a nitrile of formula (II) given hereinbelow is reacted with hydrogen sulfide, in the presence of a catalyst, a thioamide having the above formula (I) can easily be obtained.

More specifically, in accordance with this invention, there is provided a process for preparing, very easily and advantageously, adamantyl thioamide derivatives having the above formula (I) by reacting a nitrile having the formula

in which Ad, $m$ and $n$ have the same meanings as defined above, with hydrogen sulfide, in the presence of a catalyst.

The process of this invention can be worked very easily and simply. A nitrile represented by the above formula (II) is dissolved in a suitable solvent such as dimethylformamide, dimethylsulfoxide and lower alcohols, i.e. alkanols having from 1 to 3 carbon atoms, and then, the nitrile is reacted with hydrogen sulfide in the presence of a catalyst. The reaction is carried out at a temperature of 20° to 200°C., preferably 40° to 180°C.

As the catalyst, there can be employed ammonia, amines such as lower monoalkylamines, lower dialkylamines, lower trialkylamines, wherein each of said alkyls has from 1 to 4 carbon atoms, piperidine, pyrrolidine and morpholine, and alcoholates of metals of Groups I and II of the Periodic Table. Good results are obtained when the catalyst is used in an amount of 0.0002 to 5 moles, preferably 0.001 to 1.0 mole, per mole of hydrogen sulfide.

According to the invention, there are obtained compounds of the formulas

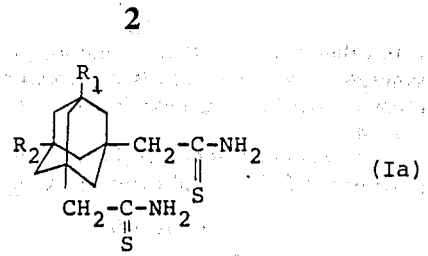

and

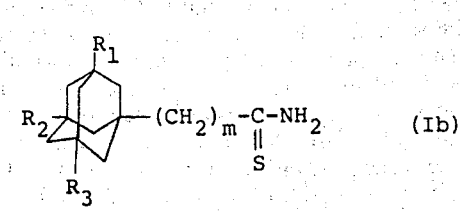

wherein $R_1$, $R_2$ and $R_3$, which can be the same or different, are hydrogen or alkyl having 1 to 4 carbon atoms, and $m$ is zero or 1.

The compounds of the above formulas (I), (Ia) and (Ib) are extremely useful as intermediates for preparing useful adamantane-substituted heterocyclic compounds and they possess very improved antiviral activity.

Many types of viral diseases are known in the field of human medicine and veterinary medicine. Such diseases include, for example, Newcastle disease, fowl pox, infectious bronchitis of fowls, viral duck hepatitis, hog cholera and infectious gastroenteritis of hogs, cow pox, foot and mouth disease and para-influenza of cattle. Preventive or therapeutic medicines for these diseases known today, either on a laboratory test basis or in practical use, are antibiotics such as tetracyclines and vaccines. However, the viruses can develop resistance to the antibiotics.

The compounds of formula (I), according to the present invention, have been found to have particularly good effects against Newcastle disease virus among Paramyxo virus belonging to RNA type in the embryo cells of fowls.

Accordingly, the present invention provides antiviral agents for use in the veterinary medicine field, and containing the compound of formula (I) as its principal effective ingredient.

In formula (I), when $n$ is one, Ad is 1-adamantyl or 1-adamantyl substituted with one, 2 or 3 alkyls having from 1 to 4 carbons at the 3, 5 or 7 bridgehead carbon atoms of the adamantane ring, such as 3-methyl-, 3,5-dimethyl-, 3,5,7-trimethyl-, and 3-ethyl-(1)-yl. When $n$ is 2, Ad is 1,3-adamantylene or 1,3-adamantylene substituted by 1 or 2 alkyls having from 1 to 4 carbon atoms at the 5 or 7 bridgehead carbon atoms of the adamantane ring, such as 5-methyl-, 5,7-dimethyl-, and 5-ethyl-adamant-(1,3)-ylene.

The formula (I) compounds possess sufficient effectiveness when used alone, but they may also be used with other chemical therapeutic agents in which case synergistic effects of the two ingredients and the decreased resistance gained by the virus will become evident.

This invention will now be further described by reference to the following illustrative Examples.

EXAMPLE 1

Preparation of adamantyl thioacetamide (Ad is 1-adamantyl, $n$ is one, $m$ is one)

One and six tenths grams of adamantyl acetonitrile was dissolved in 40 ml of dimethylformamide, and 0.73 g of diethylamine was added to the solution. While the mixture was maintained at 60°C., hydrogen sulfide was bubbled into the mixture at a rate of 35 ml/min for 4 hours. Then, the reaction mixture was stirred at the above tempeature for 3 hours to complete the reaction. The reaction mixture was cooled to room temperature and added to dilute hydrochloric acid aqueous solution. The precipitate was removed by filtration, and the filtrate was extracted with diethyl ether. The ether extract was washed with water and dried, and diethyl ether was distilled off. The solid residue was combined with the above precipitate, and the combined solids were washed with petroleum ether to obtain 2.0 g (yield = 95%) of adamantyl thioacetamide. Recrystallization from ethanol gave a pure product.

Elemental Analysis Values:
Found: C, 69.0%; H, 9.2%; N, 6.4%; S, 15.4%;
Calculated: C, 68.85%; H, 9.15%; N, 6.69%; S, 15.31%

Melting Point: 185°–186°C.

EXAMPLE 2

Preparation of 1,3-bis(aminothiocarbonylmethyl)adamantane (Ad is adamant-(1,3)-ylene, $n$ is 2, $m$ is one)

Five and four hundredths grams of 1,3-bis(cyanomethyl)adamantane was dissolved in 50 ml of dimethylformamide, and 3.85 g of diethylamine was added to the solution. While the mixture was maintained at 50°C., hydrogen sulfide was bubbled into the mixture at a rate of 40 ml/min for 4.5 hours, and then the reaction mixture was stirred at the same temperature for 3 hours to complete the reaction. The reaction mixture was cooled to room temperature and added to dilute hydrochloric acid aqueous solution. The precipitate was recovered by filtration and washed with diethyl ether to obtain 6.2 g (yield = 93%) of 1,3-bis(aminothiocarbonylmethyl)adamantane. Recrystallization from ethanol gave a pure product.

Elemental Analysis Values:
Found: C, 59.0%; H, 7.6%; N, 9.8%; S, 23.1%.
Calculated: C, 59.53; H, 7.85%; N, 9.92%; S, 22.70%.

Melting Point: 186°–188°C.

EXAMPLE 3

Preparation of adamantylthioamide (Ad is 1-adamantyl, $n$ is one, $m$ is zero)

Three and two tenths grams of adamantyl nitrile was dissolved in 30 ml of dimethylformamide and then 1.54 g of diethylamine was added to the solution. While the mixture was maintained at 50°C, hydrogen sulfide was bubbled into the mixture at a rate of 20 ml/min. for 5 hours. Then, the reaction mixture was stirred at the above temperature for 2 hours to complete the reaction. The reaction mixture was cooled to room temperature and was added to dilute hydrochloric acid aqueous solution. The precipitate thus obtained was removed by filtration and it was washed with water. Then, it was dried to obtain g (yield = 90%) of adamantyl thioamide. Recrystallization from ethyl alcohol gave the pure product.

Elemental Analysis Values:
Found: C, 67.5%; H, 8.8%, N, 7.4%, S, 16.0%.
Calculated: C, 67.64%; H, 8.77%; N, 7.17%; S, 16.41%.

Melting Point: 195°–197°C.

EXAMPLE 4

Chick embryo fibroblasts were cultured for 2 to 3 days in a test tube according to the monolayer culture method and were inoculated with Newcastle disease virus of about 128 HAU (hemagglutination units). A culture medium of the stepwise dilution system containing a compound as listed below was added to the upper layer and the culturing was continued for 48 hours at 37°C. The antiviral effect was evaluated based on the hemagglutination reaction. The results obtained are shown below.

| Compound | Concentration ($\mu$g/ml) | % HAU* | CT** |
|---|---|---|---|
| adamantyl thioacetamide | 625 | below 0.9 | ± |
|  | 500 | below 0.9 | ± |
|  | 250 | 20 | ± |
|  | 100 | 20 | − |
|  | 50 | 14 | − |
|  | 25 | 40 | − |
|  | 2.5 | 100 | − |
| 1,3-bis(aminothiocarbonyl-methyl)adamantane | 500 | below 5 | ± |
|  | 250 | 56 | − |
|  | 100 | 100 | − |
|  | 50 | 100 | − |
| adamantylthioamide | 500 | below 5 | ± |
|  | 250 | 20 | − |
|  | 100 | 68 | − |
|  | 50 | 100 | − |
| adamantylamine hydrochloride (comparative compound) | 1000 | below 1 | ++ |
|  | 500 | below 1 | + |
|  | 250 | 9 | ± |
|  | 125 | 100 | − |
|  | 62 | 100 | − |

-continued

Notes:

*: % HAU = $\dfrac{\text{HAU in sample containing test compound (dilution times inhibiting hemagglutination)}}{\text{HAU in untreated sample}} \times 100$

**: CT indicates the degree of the damage to chick embryo cells by the test compound.
− : no damage
± : small eruptions were formed on the cell surface
+ : cells of the monolayer parted from the tube wall
++ : cells were rounded or destroyed The embodiment of the invention in which an exclusive property or privilege is claimed are defined as follows:

1. 1,3-bis(aminothiocarbonylmethyl)adamantane.

* * * * *